(12) United States Patent
Nowakowska et al.

(10) Patent No.: US 9,925,215 B1
(45) Date of Patent: Mar. 27, 2018

(54) ANIONICALLY MODIFIED POLYALLYLAMINE DERIVATIVE, USE OF ANIONICALLY MODIFIED POLYALLYLAMINE DERIVATIVE AS MEDICINE, PARTICULARLY FOR PROPYLAXIS AND TREATMENT OF INFECTIONS OF RESPIRATORY TRACT CAUSED BY HUMAN METAPNEUMOVIRUS (HMPV), HUMAN RHINOVIRUSES (HRV), AND INFECTION BY INFLUENZA VIRUS TYPE A (IAV) AND PHARMACEUTICAL COMPOSITION COMPRISING THE ANIONICALLY MODIFIED POLYALLYLAMINE DERIVATIVE

(71) Applicant: UNIWERSYTET JAGIELLONSKI, Cracow (PL)

(72) Inventors: Maria Nowakowska, Cracow (PL); Krzysztof Szczubialka, Krzywaczka (PL); Krzysztof Pyrc, Cracow (PL); Justyna Ciejka, Mogilany (PL); Magdalena Wytrwal, Cracow (PL); Aleksandra Milewska, Cracow (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 0 days.

(21) Appl. No.: 15/792,962

(22) Filed: Oct. 25, 2017

Related U.S. Application Data

(62) Division of application No. 15/329,324, filed as application No. PCT/IB2015/055727 on Jul. 29, 2015.

(30) Foreign Application Priority Data

| Jul. 29, 2014 | (PL) | ................................. 409015 |
| Jul. 29, 2014 | (PL) | ................................. 409016 |
| Jul. 8, 2015 | (PL) | ................................. 413055 |

(51) Int. Cl.
*A61K 31/795* (2006.01)
*C08F 126/02* (2006.01)

(52) U.S. Cl.
CPC .......... *A61K 31/795* (2013.01); *C08F 126/02* (2013.01)

(58) Field of Classification Search
None
See application file for complete search history.

(56) References Cited

U.S. PATENT DOCUMENTS

| 2002/0025919 A1 | 2/2002 | Matthews et al. ............... 514/2 |
| 2004/0229219 A1 | 11/2004 | Gallaher et al. ............... 435/5 |
| 2015/0011003 A1* | 1/2015 | Kuriyama ............ C12N 5/0663 435/377 |

FOREIGN PATENT DOCUMENTS

| CA | 2868718 | 10/2013 | ............ C12N 1/00 |
| JP | S62-53665 A | 3/1987 | ............ A61L 3/00 |
| JP | S62-57562 A | 3/1987 | ............ A61L 33/00 |
| JP | S62-57613 A | 3/1987 | ............ B01D 13/04 |

OTHER PUBLICATIONS

International Search Report dated Sep. 14, 2016 in related application No. PCT/IB2015/055727.
Written Opinion dated Sep. 14, 2016 in related application No. PCT/IB2015/055727.
Search Report dated May 14, 2015 in related application No. P.409015.
Search Report dated May 14, 2015 in related application No. P.09016.
Search Report dated Oct. 21, 2015 in related application No. P.413055.
Artyushenko et al.; *Study of Interaction of Polystyrene Sulfonate with Polymerization Degree of 8 and Polyallylamine with Bilayer Lipids Membranes*; Biophysics, Jun. 2012; vol. 57, No. 2; pp. 179-180.
Ikeda et al.; *In Vitro and In Vivo Inhibition of Ortho- and Paramyxovirus Infections by a New Class of Sulfonic Acid Polymers Interacting with Vicus-Cell Binding and/or Fusion*; Antimicrobial Agents and Chemotherapy; American Society for Microbiology; Feb. 1994; vol. 38, No. 2; pp. 256-259.
Iarikov et al.; *Antimicrobial Surfaces Using Covalently Bound Polyallylamine*; ACS, BioMacromolecules; 2014; vol. 15; pp. 169-176.
Lotz et al.; *Antimicrobial efficacy and optimized cell adhesion from defined plasma polymerized multilayer structures involving zinc acetylacetonate and allylamine*; Journal of Materials Chemistry; 2012; vol. 22; pp. 19455-19461.
Holme et al.; *Chitosan N-sulfate, A water-soluble polyelectrolyte*; Carbohydrate Research; Jul. 1997; vol. 302, Issues 1-2; pp. 7-12.
Artyushenko et al.; *Influence of polyelectrolytes on measles virus infectivity*; Journal of Microbiology, Epidemiology and Immunobiology; Jul.-Aug. 2011; vol. 4; pp. 36-40.
Milewska et al.; *Novel polymeric inhibitors of HCoV-NL63*; Antiviral Research; 2013; vol. 97; pp. 112-121.
Office Action dated Jun. 1, 2017 in related U.S. Appl. No. 15/329,324.
Response filed Aug. 28, 2017 in related U.S. Appl. No. 15/329,324.

* cited by examiner

*Primary Examiner* — Brian Gulledge
(74) *Attorney, Agent, or Firm* — Renner Kenner Greive Bobak Taylor & Weber

(57) ABSTRACT

The subject of the invention is an N-sulfonic polyallylamine derivative (NSPAH) with Formula 1, wherein R is $-SO_3^-$ or $-H$, and n is an integer from 150 to 15000; an application of the N-sulfonic polyallylamine derivative as a medicine, particularly for prevention and treatment of respiratory tract infections caused by the human metapneumovirus (hMPV), respiratory tract infections caused by the human rhinoviruses (HRV), and infections caused by the influenza A virus; as well as a pharmaceutical composition comprising the N-sulfonic polyallylamine derivative and application thereof.

3 Claims, 8 Drawing Sheets

ANIONICALLY MODIFIED POLYALLYLAMINE DERIVATIVE, USE OF ANIONICALLY MODIFIED POLYALLYLAMINE DERIVATIVE AS MEDICINE, PARTICULARLY FOR PROPYLAXIS AND TREATMENT OF INFECTIONS OF RESPIRATORY TRACT CAUSED BY HUMAN METAPNEUMOVIRUS (HMPV), HUMAN RHINOVIRUSES (HRV), AND INFECTION BY INFLUENZA VIRUS TYPE A (IAV) AND PHARMACEUTICAL COMPOSITION COMPRISING THE ANIONICALLY MODIFIED POLYALLYLAMINE DERIVATIVE

CROSS-REFERENCE TO RELATED APPLICATION

This is a Divisional of application Ser. No. 15/329,324 filed Jan. 26, 2017, which is a § 371 application of International Patent Application No. PCT/IB2015/055727, filed Jul. 29, 2015, which claims benefit of Polish Patent Application Nos. PL409015 filed Jul. 29, 2014; PL409016 filed Jul. 29, 2014; and PL413055 filed Jul. 8, 2015, and which is incorporated herein by reference.

TECHNICAL FIELD

The invention relates to an anionically modified polyallylamine, an N-sulfonic polyallylamine derivative, application of the N-sulfonic polyallylamine derivative as a medicine, particularly for prevention and treatment of respiratory tract infections caused by human metapneumovirus (hMPV) and human rhinovirus (HRV), as well as infections with influenza A virus (IAV), and to a pharmaceutical composition comprising the N-sulfonic polyallylamine derivative and the application thereof.

BACKGROUND OF INVENTION

The human metapneumovirus (hMPV), described for the first time in 2001, belongs to the Paramyxoviridae family, Pneumovinae subfamily, *Pneumovirus* genus. Similarly to the influenza virus or the human respiratory syncytial virus (hRSV), it causes respiratory tract diseases, though with a milder course. The hMPV is responsible for 7-8% of viral diseases of the respiratory tract among children and 2-3% among adults [1], attacking ciliated epithelial cells of the respiratory tract. A disease caused by the human metapneumovirus has influenza-like symptoms (rhinitis, cough, fever). The virus is widespread on all continents, and the highest frequency of its occurrence in observed in winter and spring. It is characterised by droplet infection [2]. More severe symptoms, including serious infections of the lower respiratory tract, are found mainly with children and infants under the age of five [1][2], with elderly people above the age of sixty and with persons having a reduced immunity level [2].

As the American Lung Association and the latest reviews on the subject report, no medicine inhibiting or preventing infections caused by the hMPV has been approved for use hitherto [1,2,3,4,5]. Till 2012, only ribavirin ((1-β-D-ribofuranosyl-1,2,4-triazole-3-carboxamide)—a nucleoside being a guanosine analogue—exhibiting a broad range of actions against various viruses (RNA, DNA) of the respiratory tract [2,4,5], and immunoglobulins [2,5] were used for treatment of very severe acute infections caused by the hMPV among patients with lung transplants. However, they were used only in critical cases, because of their undesirable effects and potential teratogenic activity [2,4].

Till now, a method for inhibition of hMPV replication by using peptides was disclosed, the peptides exhibiting a strong affinity to viral fusion protein F, thus blocking the lifecycle of the human metapneumovirus already at the stage of its fusion to host cells (Patent Application No. US20040229219A1, *Method of inhibiting human metapneumovirus and human coronavirus in the prevention and treatment of severe acute respiratory syndrome* (SARS), 2004). Other patent documents relate to prevention and inhibition of the hMPV by using proper antibodies or recombined human metapneumoviruses (application as vaccines).

SUMMARY OF INVENTION

The human rhinovirus (HRV) belongs to the Picornaviridae family. These viruses do not have a glycoprotein envelope, and their genetic material is constituted by a single RNA strand with a positive polarity. HRV virions belong to the smallest known viruses, and their diameter does not exceed 30 nm. During the year, particularly in winter and spring, they cause infections of the upper respiratory tract with humans, appearing as the common cold. As the medical website Medscape reports, these viruses are the cause of up to 25-80% of all infection cases. In spite of the fact that they are mainly linked with the common cold, rhinoviruses also cause otitis media, sinusitis and inflammations of the lower respiratory tract, including bronchiolitis, bronchitis and pneumonia [7]. With children, they may cause wheezing and asthma exacerbations as well [7,8].

In spite of the fact that these viruses are the cause of so frequent infections of the upper respiratory tract with humans, development of an effective vaccine preventing these infections is not possible. The main problem is human rhinoviruses occur as a great many serotypes (more than 100 HRV serotypes are known [9]). Moreover, there are no known commercially available medicines at present which would inhibit replication of human rhinoviruses. Literature references indicate the possibility of using α-2b interferon—a glycoprotein with activity based on enhancing the immune response of the organism, or a recombined ICAM-1 protein, being a synthetic analogue of receptors on the surface of the host cells, used by viruses to attach to these cells [10]. Pleconaril and Pirodavir, two synthetic low-molecular compounds, seemed to be the most promising inhibitors of HRV replication [11]. The compounds attach to the hydrophobic part of the HRV virion capsid, precluding the subsequent liberation of the viral RNA, thus preventing initiation of the virus replication cycle. Unfortunately, because of their side effects, these substances were not accepted by the Food and Drug Administration (FDA) for oral common cold treatment [12]. Grassauer et al. proved in their paper that iota-carrageenan exhibits antirhinoviral activity, the compound belonging to polysaccharides containing sulfate groups. The authors suggest that iota-carrageenan could also find application in prevention and treatment of common colds caused by the rhinoviruses [13]; however, as a result of its strong propensity to form gels and the low solubility resulting from this, the usefulness of carrageenans as antirhinoviral agents seems to be limited.

The influenza A virus (IAV) causes respiratory tract infections with an acute and severe course. It is one of the most clinically significant pathogens of the respiratory tract. Influenza virus infections occur most often in winter (seasonal influenza, the highest incidence being in January-February [1]). The World Health Organisation (WHO) estimates that there are 3-5 million cases of influenza yearly, including 250-500 thousand fatal cases [14,15]. The most severe infections occur with children under the age of two, elderly people above the age of sixty-five and with persons having a reduced immunity level. The WHO recommends vaccination against influenza viruses as the most effective method for prevention of infection [16]. The emergence of new types of the virus may lead to the development of an epidemic or a pandemic. The high variability of the virus, difficulties in rapidly obtaining an adequate number of vaccines before the epidemic wave and occasional insufficient effectiveness of the vaccine results in the fact that this disease still constitutes a significant medical and epidemiological problem.

The anti-influenza medicines currently used affect one of two stages of the replication cycle of the influenza virus. Namely, they disturb the stage of removal of the protein envelope of the virus after it penetrates the cell by blocking the ion channels of the M2 protein (Amantadine and Rimantadine), or they inhibit liberation of new virus molecules from the infected cell by affecting neuraminidase (NA), a viral envelope protein responsible, most of all, for the liberation of the newly formed influenza virus molecules from the infected cells (Zanamivir and Oseltamivir) [17-21]. The envelope of the influenza virus also contains haemagglutinin (HA)—a glycoprotein responsible, most of all, for the process of attachment and penetration of the interior of epithelial cells in the respiratory tract by the virions, and thus for the initiation of infections. Haemagglutinin-blocking anti-influenza medicines include high-molecular drugs—peptides and proteins, e.g. EB (entry blocker) peptide, attaching specifically to HA, preventing a repeated infection. NDFRSKT peptide exhibits a high antiviral activity and—similarly to the EB peptide—inhibits HA activity. The principle of operation of another peptide, FLUDASE, is different, as the inhibition occurs by a removal of the receptor (sialic acid residue) from the surface of the host cells, thus precluding attachment and cell penetration of the virions [21]. Unfortunately, high genetic variability leads to rapid adaptation of the pathogen to the environment and the emergence of strains resistant to the therapy. For example, M2 protein inhibitors are already ineffective and not used. Similarly, strains of the influenza virus resistant to hitherto used neuraminidase-blocking medicines, i.e. Oseltamivir and Zanamivir, have already emerged. In this connection, new neuraminidase inhibitors—Laninamivir, Favipiravir and Peramivir—have been introduced lately in Japan and South Korea. Laninamivir, administered only by inhalation, effectively inhibits infections caused by viruses resistant to Oseltamivir, while Peramivir, administered intravenously, is particularly useful in the treatment of patients who cannot take Zanamivir (e.g. patients affected with asthma) infected with an influenza virus strain resistant to Oseltamivir [21]. One may find information in literature that also carrageenans interact with particles of the influenza virus directly, precluding its absorption and cell penetration [20,22,23,24].

The goal of the invention was to develop a substance inhibiting replication of the human metapneumovirus (hMPV), the human rhinovirus (HRV) and the influenza A virus (IAV), which would find application in prevention or therapy of infections caused by these viruses in human organisms.

Surprisingly, it was discovered that this goal is achieved by a polyallylamine derivative anionically modified by substitution of a hydrogen atom in the amine group with a sulfonic group (NSPAH), having Formula 1 presented below.

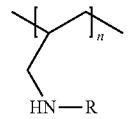

Formula 1

Anionically modified polyallylamine NSPAH

R = —SO$_3^-$ or —H wherein each R is independently selected from such groups as —SO$_3^-$ and —H, and at least one R is the —SO$_3^-$ group, and n is an integer from 150 to 15000.

Thus, the invention relates to the anionically modified N-sulfonic polyallylamine derivative (NSPAH) with Formula 1

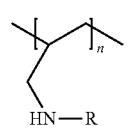

Formula 1

R = —SO$_3^-$ or —H wherein each R is independently selected from such groups as —SO$_3^-$ and —H, and at least one R is the —SO$_3^-$ group, and n is an integer from 150 to 15000.

Preferably, the N-sulfonic polyallylamine derivative is in the form of a sodium salt.

The invention then relates to the anionically modified N-sulfonic polyallylamine derivative (NSPAH) with Formula 1

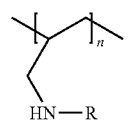

Formula 1

R = —SO$_3^-$ or —H wherein R is —SO$_3^-$ or —H, and n is an integer from 150 to 15000 to be used as a medicine, particularly to be used in therapy and prevention of infections caused by the human metapneumovirus hMPV, respiratory tract infections caused by the human rhinoviruses (HRV) and infections caused by the influenza A virus.

The invention also relates to a pharmaceutical composition, characterised in that it contains the N-sulfonic polyallylamine derivative according to the invention as an active substance.

The invention also relates to the aforementioned pharmaceutical composition to be used as a medicine, particularly to be used in therapy and prevention of infections caused by the human metapneumoviruses hMPV, respiratory tract infections caused by the human rhinovirus (HRV) and infections caused by the influenza A virus.

Preferably, this composition is in the form of a solution or an aerosol administered to the upper respiratory tract.

The invention also relates to application of the N-sulfonic polyallylamine derivative according to the invention for production of a medicine to be used in therapy and prevention of infections caused by the human metapneumovirus hMPV, respiratory tract infections caused by the human rhinoviruses (HRV) and infections caused by the influenza A virus, while preferably, the N-sulfonic polyallylamine derivative according to the invention is used for production of a medicine having the form of a solution or an aerosol administered to the upper respiratory tract.

THE SUBJECT OF THE INVENTION IS PRESENTED IN MORE DETAIL IN THE FOLLOWING EMBODIMENTS

Example 1

Preparation and Physico-Chemical Characterisation of the Anionic Polyallylamine Derivative (NSPAH)

The reaction of the polyallylamine modification, shown in Scheme 1, was used earlier for preparation of an N-sulfonic chitosan derivative [6].

Scheme 1. Reaction of the N-sulfonic polyallylamine derivative (NSPAH) preparation.

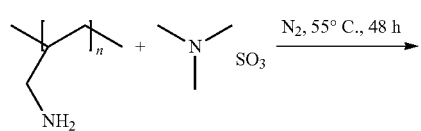

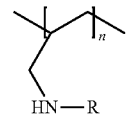

$R = \text{---} SO_3^-$ or $\text{---} H$ 0.5 g of polyallylamine hydrochloride (PAH-15) with a molecular mass of Mw ~15 kDa or 2.45 ml of 20% polyallylamine hydrochloride solution (PAH-65) with a molecular mass of Mw ~65 kDa were dissolved in 25 ml of distilled water. 1.85 g of sodium carbonate was then added, and the mixture was stirred using a magnetic stirrer for 45 minutes in order to unlock the amine groups. During this time, the mixture was degassed by passing nitrogen through the system and afterwards a proper amount (Table 1) of sulfur trioxide-trimethylamine complex (STTC). The reaction was carried out for 48 hours at 55° C., with the mixture being stirred using a magnetic stirrer. After this time, the reaction mixture was cooled to room temperature and dialysed against water for 7 days. The obtained polymers were isolated from the solutions by freezing in a freeze dryer for 48 hours.

Figure 1:
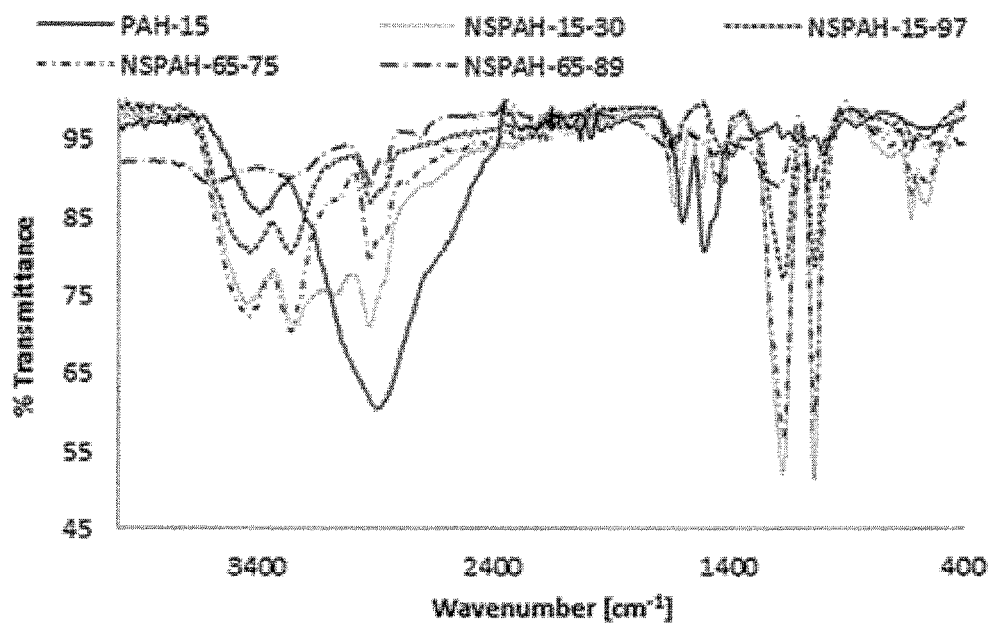
FIG. 1 shows FTIR-ATR spectra of the polyallylamine before (PAH-15-0—solid line) and after modification (NSPAH-15-30, NSPAH-15-95, NSPAH-65-75, NSPAH-65-89—dashed lines).
Figure 2A:
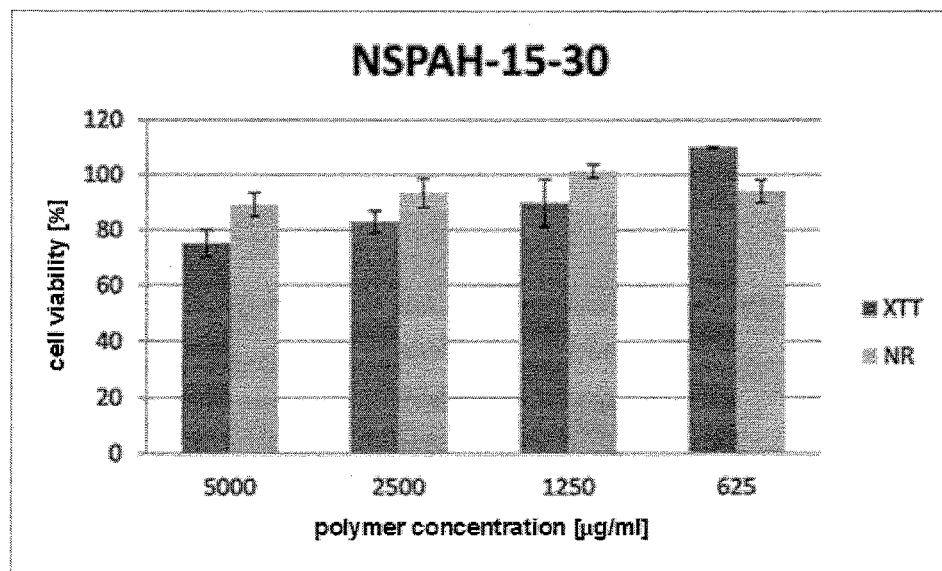
FIGS. 2a, 2b, 2c and 2d show the results of a cytotoxicity study of NSPAH-15-30, NSPAH-15-95, NSPAH-65-75 and NSPAH-65-89 polymers, respectively, carried out on the LLC-MK2 cell line by XTT and NR tests.
Figure 2B:
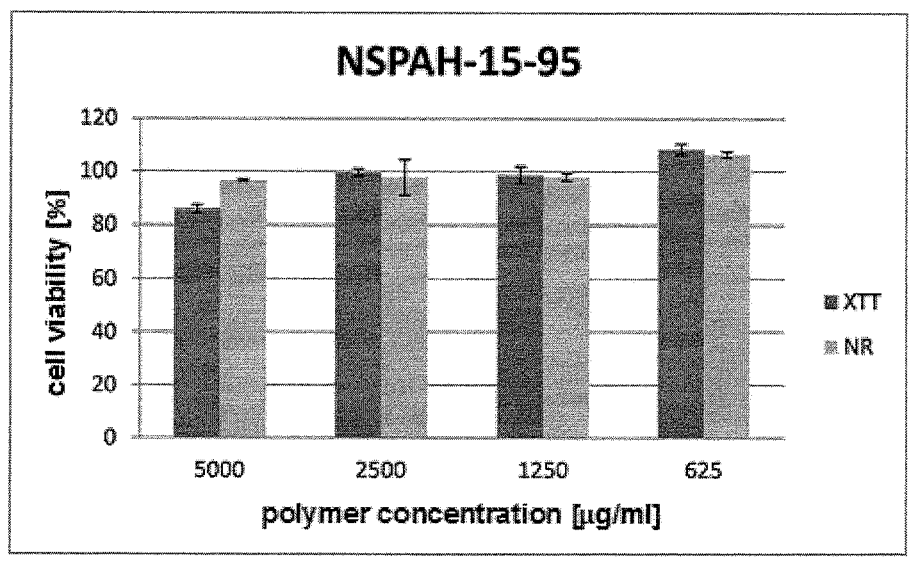
Figure 2C:
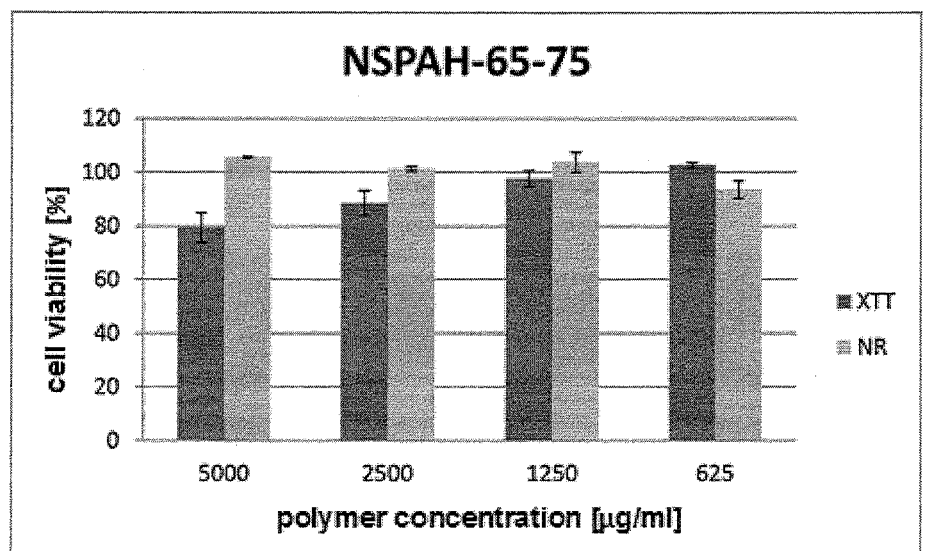
Figure 2D:
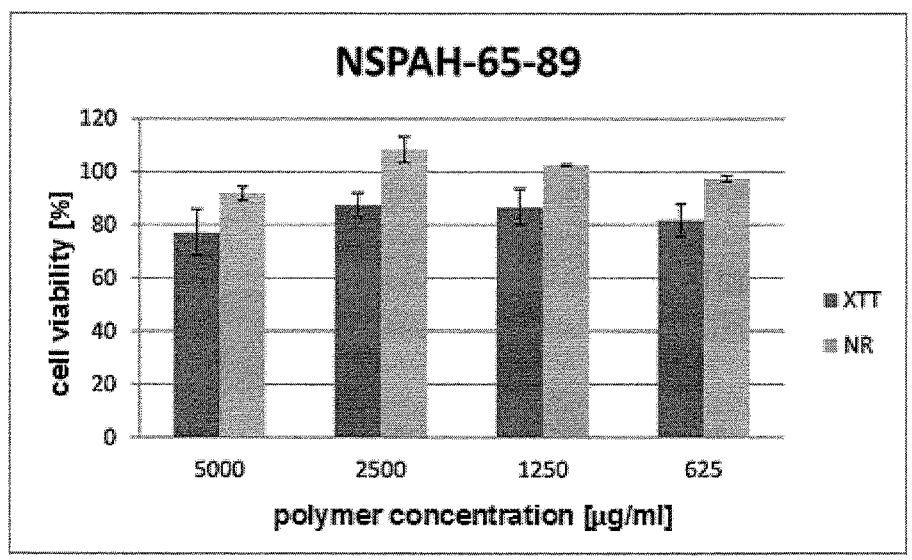
Figure 3A:
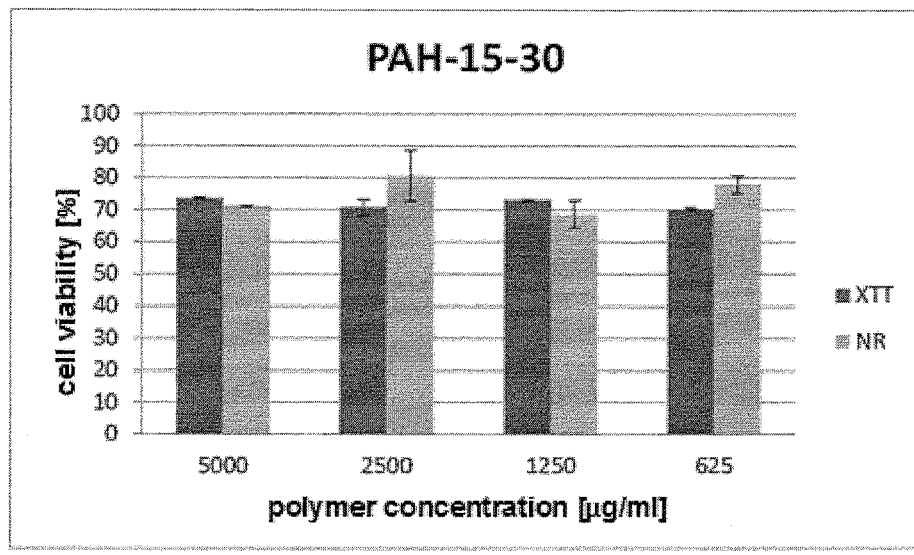
FIGS. 3a, 3b, 3c and 3d show the results of a cytotoxicity study of NSPAH-15-30, NSPAH-15-95, NSPAH-65-75 and NSPAH-65-89 polymers, respectively, carried out on the MDCK cell line (Madin-Darby dog kidney cells) by XTT and NR tests.
Figure 3B:
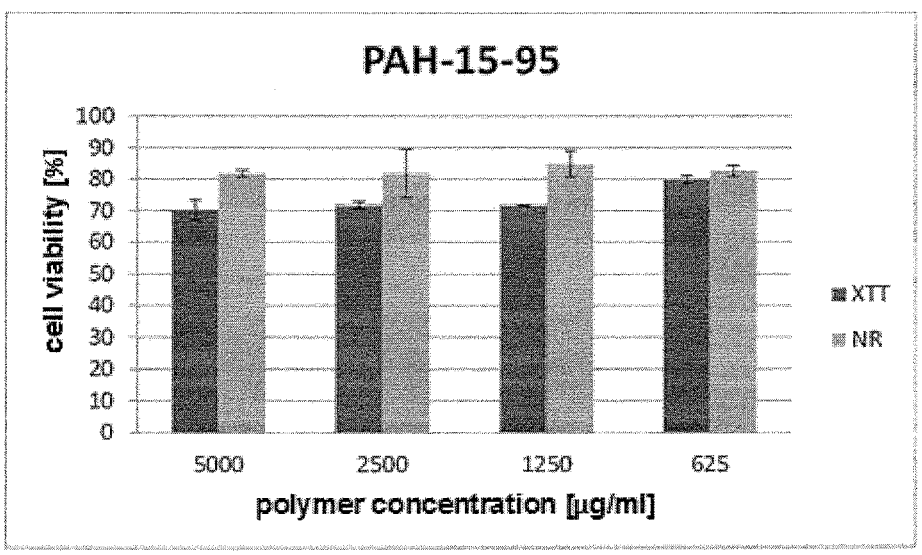
Figure 3C:
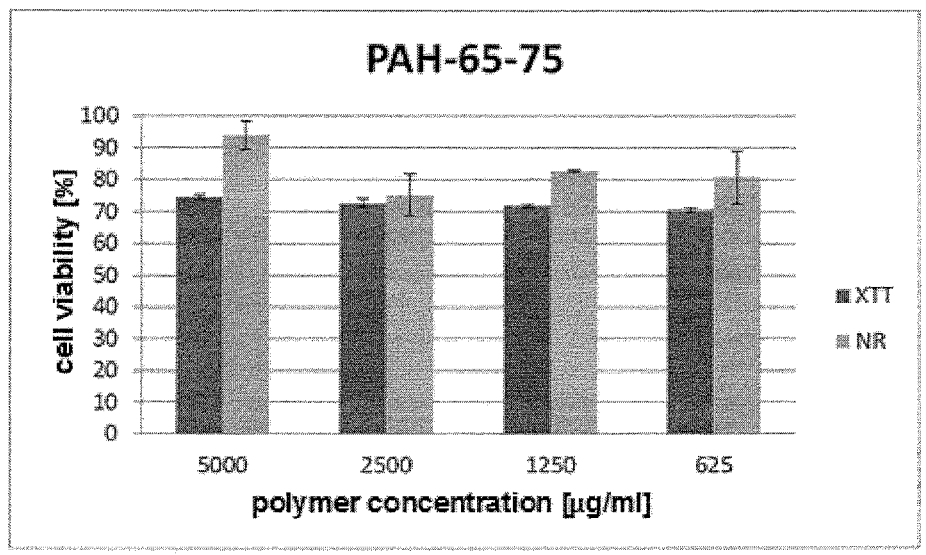
Figure 3D:
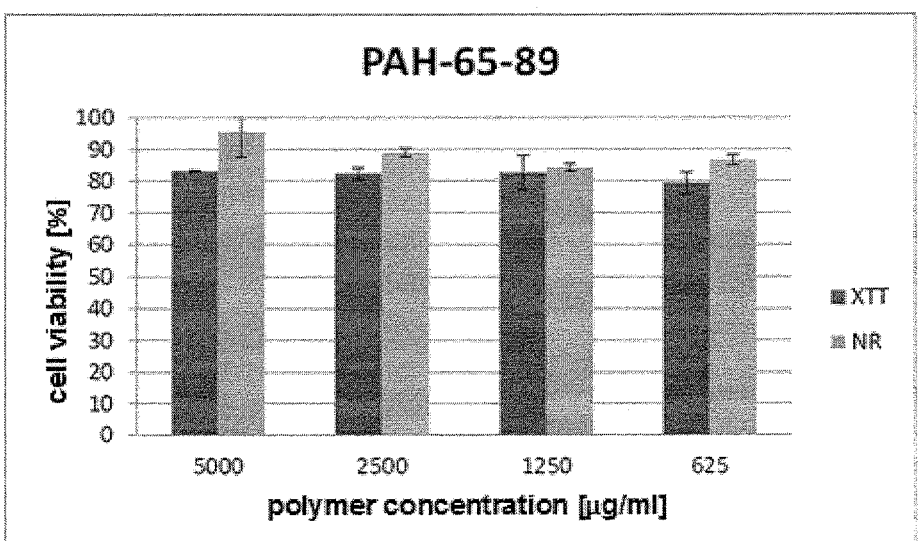

The structure of the anionically modified polyallylamines is confirmed by FTIR-ATR spectra (FIG. 1). Values of the degree of substitution are collected in Table 1.

In the FTIR-ATR spectra of the modified polyallylamines, bands at 631-662, 1044-1086 and 1211-1198 cm$^{-1}$ occur, characteristic for stretching vibrations of sulfonic moieties present in the modified polyallylamine.

The degree of substitution (DS) with sulfonic groups was calculated based on the results of elemental analysis. The degree of substitution and zeta potential of the obtained polymers are presented in Table 1.

TABLE 1

Reaction conditions, composition and physico-chemical characteristics of the synthesised N-sulfonic polyallylamines.

| Polymer | STTC/amine groups molar ratio | DS [%][a] | zeta potential [mV][b] PBS buffer pH = 7.4 | zeta potential [mV][c] medium 0% DMEM |
|---|---|---|---|---|
| — | — | — | — | −5.1 ± 0.5 |
| PAH-15-0 | — | 0 | +26.4 ± 1.4 | +7.0 ± 0.6 |
| PAH-65-0 | — | 0 | +4.3 ± 0.5 | — |
| NSPAH-15-95 | 5.0 | 95 | −11.5 ± 0.4 | −15.2 ± 0.6 |
| NSPAH-56-98 | 5.0 | 98 | −13.6 ± 2.2 | −24.4 ± 1.6 |
| NSPAH-65-89 | 5.0 | 89 | −16.7 ± 0.8 | −30.0 ± 0.7 |

[a]The degree of substitution with sulfonic groups calculated based on elemental analysis. The DS is a percentage of amine groups substituted with the sulfonic group; therefore, e.g., DS = 30% means that in 30% of amine groups in allylamine units, one H atom was replaced with the SO$_3^-$ moiety.
[b]polymer concentration 0.5 mg/ml, temperature 25° C.; average of 5 measurements.
[c]polymer concentration 0.5 mg/ml, temperature 25° C.; average of 5 measurements.

Example 2

Cytotoxicity of the Studied Polymers

The cytotoxicity of anionically modified polyallylamines towards LLCMK2 cells (*Macaca mulatta* monkey kidney cells) and MDCK cells (dog kidney cells) (FIGS. 2, 3) was examined.

The cytotoxicity was determined based on two tests. The first test consisted of a colorimetric test based on the ability of mitochondrial enzymes (succinate dehydrogenase) to reduce the XTT dye ((2,3-bis-(2-methoxy-4-nitro-5-sulfophenyl)-2H-tetrazolium-5-carboxanilide) to coloured Formazan salts. Determination of the number and condition of cells may be done based on the existence of a direct dependence between cell viability and the amount of dye formed, calculated from an absorbance measurement at the absorption maximum (450 nm) (FIGS. 2, 3).

Evaluation of cell viability was also carried out using neutral red (NR). The test is based on the ability of neutral red to pass to the cytoplasm via passive transport. The dye accumulates in the lysosomes of living cells. The percentage of living cells is calculated after a lysis of cells and absorption measurements of the obtained solutions at 540 nm (FIGS. 2, 3).

In the case of the LLC-MK2 line culture, the cells were grown for 6 days in a medium defined with DMEM without serum, but with an addition of trypsin, a medium containing the studied sulfonic polyallylamines in increasing concentrations. After this time, the cytotoxicity of the studied substances was determined according to the methods described above. Moreover, morphological changes in the cells in the presence of the polymers were observed using a phase contrast microscope. For the concentrations used, i.e. 5000, 2500, 1250 and 625 µg/ml, a cytotoxicity level of 50% was not achieved for any of the studied polymers. In other words, the studied sulfonic polyallylamines are not toxic for the LLC-MK2 cells. FIGS. 2a, 2b, 2c and 2d show the results of a cytotoxicity study of NSPAH-15-30, NSPAH-15-95, NSPAH-65-75 and NSPAH-65-89 polymers, respectively, carried out on the LLC-MK2 cell line by XTT and NR tests. The results obtained from the measurements carried out were consistent with the observations concerning the lack of changes in cell morphology.

In the case of the MDCK line culture, the cells were incubated for 2 days in a medium defined with DMEM without serum containing the studied N-sulfonic polyallylamine derivatives in increasing concentrations. After this time, the cytotoxicity of the studied substances was determined using the methods described above. Moreover, morphological changes in the cells in the presence of the polymers were observed using a phase contrast microscope. For the concentration range of 625-5000 µg/ml, a cytotoxicity level of 50% was not achieved for any of the studied polymers. Therefore, it was proven that the studied N-sulfonic polyallylamine derivatives are not toxic for MDCK cells.

FIGS. 3a, 3b, 3c and 3d show the results of a cytotoxicity study of NSPAH-15-30, NSPAH-15-95, NSPAH-65-75 and NSPAH-65-89 polymers, respectively, carried out on the MDCK cell line by XTT and NR tests.

The results obtained from the measurements carried out were consistent with the observations concerning the lack of changes in cell morphology.

Example 3

Influence of the Studied Polymers on Inhibition of the Cytopathic Effect Caused by Replication of the Human Metapneumovirus (hMPV)

Inhibition of replication of the human metapneumovirus by sulfonic polyallylamines was examined. It was observed that the antiviral effect was stronger the higher the degree of substitution of the polyallylamine with sulfonic groups and the higher the molecular mass of the polymer was.

The experiment was carried out by infecting susceptible cells—the LLC-MK2 line—with the human metapneumovirus in the presence of the polymers in increasing concentrations. The cells were in a medium defined with DMEM without bovine serum, but with an addition of trypsin, for the entire time. After two hours of incubation at 37° C., the non-bound virions were washed out by triple rinsing of the cells with a PBS solution, and solutions of polymers with proper concentrations were then introduced. The infected cells were incubated at 37° C. for 6 days.

After the assigned incubation time, morphological changes were observed using a phase contrast microscope. Inhibition of hMPV replication and no cytopathic effect (CPE) were observed with the polymer concentrations presented in Table 2.

TABLE 2

Values of the polymer concentrations, above which inhibition of hMPV replication and no CPE were observed.

| Virus | Polymer | Minimum polymer concentration with which CPE was not observed [µg/ml] |
|---|---|---|
| hMPV | NSPAH-15-30 | >2000 |
|  | NSPAH-15-95 | 1000 |
|  | NSPAH-65-75 | 500 |
|  | NSPAH-65-89 | 500 |

Example 4

Study on the Influence of Sulfonic Polyallylamines on hMPV Replication In LLC-MK2 Cells Using RT-PCR Real-Time Analysis.

The influence of sulfonic polyallylamines on hMPV replication was examined by a measurement of the number of RNA copies in the medium using real-time RT-qPCR analysis (Reverse Transcription Quantitative Polymerase Chain Reaction). In the study, the LLC-MK2 cells were incubated for 6 days in a medium defined with DMEM without bovine serum, but with an addition of trypsin. The infection was carried out in the presence of the polymer; after 2 hours of incubation of the cells with the virus, the medium was removed, and a fresh medium comprising polymers with proper concentrations was then introduced. The incubation was continued for 6 days. When the incubation was completed, total RNA was isolated from the cell supernatants. After the reverse transcription reaction, cDNA was used as a matrix for the PCR.

Figure 4:
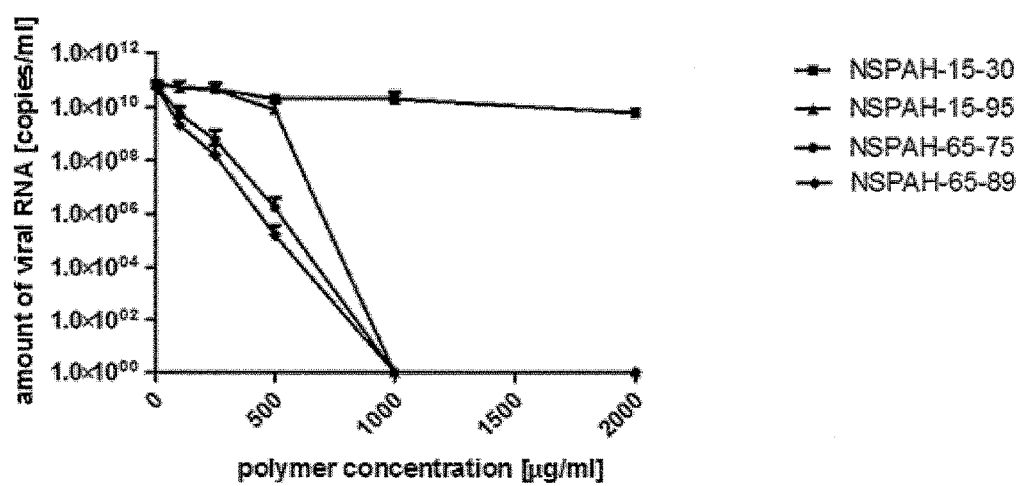
FIG. 4 shows the inhibition of replication of the human metapneumovirus (hMPV) by the N-sulfonic polyallylamine derivatives according to the invention, depending on the concentration, the degree of substitution with sulfonic groups and the molecular mass of the studied polymers.

The experiment was carried out using increasing concentrations of polymers. The obtained results are shown in FIG. 4, illustrating the inhibition of replication of the human metapneumovirus (hMPV) by the N-sulfonic polyallylamine derivatives, depending on the concentration, the degree of substitution with sulfonic groups and the molecular mass of the studied polymers. The number of viral RNA copies was expressed as the number of RNA copies in 1 ml of the sample.

Based on the presented dependencies, the values of concentrations of the N-sulfonic polyallylamines were determined, for which a 50% inhibition of replication of the human metapneumovirus (the so-called $IC_{50}$) occurred. These values are gathered together in Table 3. It was observed that sulfonic polyallylamines caused an inhibition of replication of the human metapneumovirus, while in the control samples (without the addition of the polymers), normal replication was found. A dependence of the antiviral effect vs. the degree of substitution with sulfonic groups and the molecular mass of the polyallylamines was proven. The studies carried out indicate that the effect is stronger the higher the molecular mass is and with the higher degree of substitution of the polymer is.

TABLE 3

Values of $IC_{50}$ determined based on the results of real-time PCR analysis (qRT-PCR).

| Polymer | Polymer concentration for $IC_{50}$ [µg/ml] |
|---|---|
| PAH-15-0 | — |
| PAH-65-0 | — |
| NSPAH-15-30 | 335.2 ± 1.21 |
| NSPAH-15-95 | 239.0 ± 1.20 |
| NSPAH-65-75 | 20.2 ± 1.02 |
| NSPAH-65-89 | 12.9 ± 1.01 |

Example 5

Influence of the Studied Polymers on Inhibition of the Cytopathic Effect (CPE) Caused by Replication of the Human Rhinovirus (HRV)

Inhibition of rhinovirus replication by anionically modified polyallylamines with molecular masses of 15 kDa, 56 kDa and 65 kDa, and a high degree of substitution with sulfonic groups, 95%, 98% and 89%, respectively, was examined.

The experiment was carried out by infecting susceptible cells—the HeLa line—with the rhinovirus in the presence of the polymers in increasing concentrations. The cells were in a medium defined with DMEM without serum for the entire time. After two hours of incubation at 32° C., the non-bound virions were washed out by triple rinsing of the cells with a PBS solution, and solutions of polymers with proper concentrations were then introduced. The infected cells were incubated at 32° C. for 2 days till the CPE occurred as a result of HRV infection.

After the assigned incubation time, morphological changes were observed using a phase contrast microscope. Inhibition of HRV replication, manifesting itself as a lack of the CPE, was observed in concentrations of the polymers equal to 1.0 mg/ml (Table 4).

TABLE 4

Values of the polymer concentrations, above which inhibition of HRV replication, manifesting itself as a lack of the CPE, was observed.

| Virus | Polymer | Polymer concentration, above which the CPE was not observed [mg/ml] |
|---|---|---|
| HRV | NSPAH-15-95 | 1.0 |
|  | NSPAH-56-98 | 1.0 |
|  | NSPAH-65-89 | 1.0 |

Example 6

Study on the Influence of Anionically Modified Polyallylamines On HRV Replication in HeLa Cells Using RT-qPRC Real-Time Analysis.

The influence of anionically modified polyallylamines on HRV replication was examined by a measurement of the number of RNA copies in the medium using real-time RT-qPCR analysis (Reverse Transcription Quantitative Polymerase Chain Reaction). In the study, the HeLa cells were incubated for 2 days in a medium defined with DMEM without bovine serum. The cells were infected with the HRV at a dose of $TCID_{50}=400$ in the presence of the polymers. After 2 hours of incubation at 32° C., the medium was removed, the cells were rinsed with a PBS solution three times, and a fresh medium comprising polymers with proper concentrations was then introduced. The incubation was continued for 2 days at 32° C., and RNA was then isolated from the cell supernatants. After the reverse transcription reaction, RNA was used as a matrix for the PCR.

Figure 5:
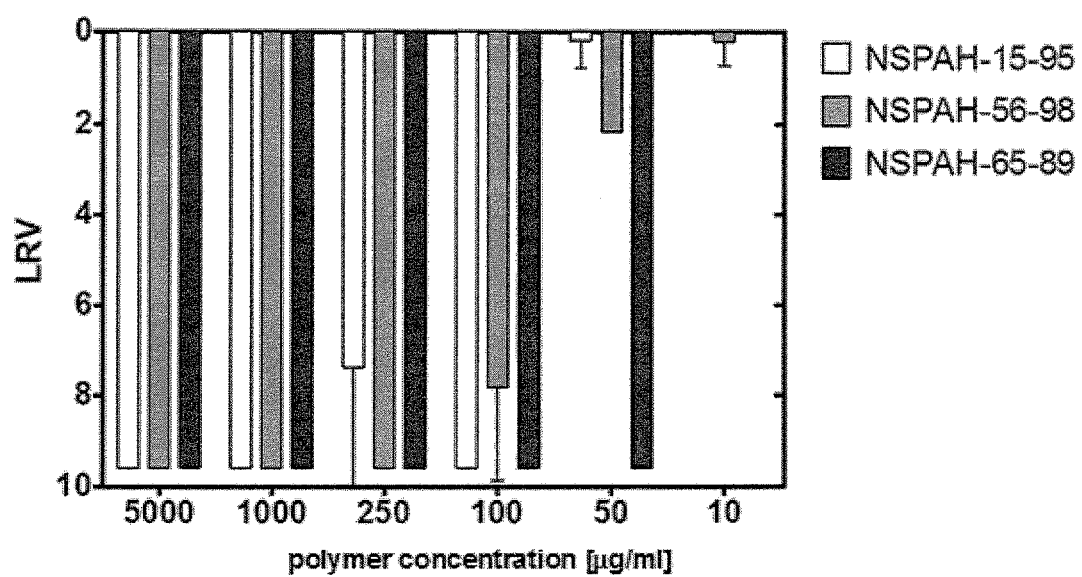
FIG. 5 shows the inhibition of replication of the human rhinovirus (HRV) by the anionically modified polyallylamine derivatives, depending on the concentration and the molecular mass of the studied polymers.

The experiment was carried out using increasing concentrations of polymers. The obtained results are shown in FIG. 5. The decrease in the number of copies of viral RNA in the studied sample in relation to the control sample, LRV (Log Reduction Value), was determined using the following formula:

$$LRV = -\log\frac{c_i}{c_0}$$

where:
$c_i$—is the number of copies of viral RNA [copies/ml] in the studied sample for a given concentration of the studied polymer;
$c_o$—is the number of copies of viral RNA [copies/ml] in the control sample, i.e. without the polymer inhibitor.

FIG. 5 shows the inhibition of replication of the human rhinovirus (HRV) by the anionically modified polyallylamine derivatives, depending on the concentration and the molecular mass of the studied polymers.

It was observed that sulfonic polyallylamines inhibit replication of the human rhinovirus very strongly (a dose of the polymers at a concentration of 100 µg/ml causes a decrease in the amount of the viral RNA in the sample to a non-measurable low value), while in the control samples (without the addition of the polymers), normal HRV replication was found. Also, a dependence between the molecular mass of the N-sulfonic polyallylamines and their antiviral activity against the HRV was proven. The studies carried out indicate that the effect is stronger the higher the molecular mass of the N-sulfonic polyallylamine derivative is.

Example 7

Influence of the Studied Polymers on the Cytopathic Effect Caused by the Influenza A Virus (IAV).

Inhibition of replication of the influenza A virus by the N-sulfonic polyallylamine derivatives was examined. It was observed that the antiviral effect was stronger the higher the degree of substitution of the polyallylamine with sulfonic groups was and the higher the molecular mass of the polymer was.

The experiment was carried out by infecting susceptible cells (MDCK) in the presence of increasing concentrations of the polymers. While infecting the cells with the IAV, they were in a medium defined with DMEM without bovine serum. After two hours of incubation at 37° C., the non-bound virions were washed out by triple rinsing of the cells with a PBS buffer, and solutions of polymers with proper concentrations were then introduced. The infected cells were incubated at 37° C. for 2 days.

After the assigned incubation time, morphological changes were observed using a phase contrast microscope. Inhibition of IAV replication and a lack of the cytopathic effect were observed already at minimum concentrations of the polymers, which is presented in Table 5.

TABLE 5

Values of the polymer concentrations, above which inhibition of IAV replication and no CPE were observed.

| Polymer | Minimum polymer concentration with which the CPE vanished [µg/ml] |
|---|---|
| NSPAH-15-30 | 1000 |
| NSPAH-15-95 | 500 |
| NSPAH-65-75 | 250 |
| NSPAH-65-89 | 250 |

Example 8

Study on the Influence of N-Sulfonic Polyallylamine Derivatives on IAV Replication in MDCK Cells Using RT-PCR Real-Time Analysis.

The influence of N-sulfonic polyallylamine derivatives on IAV replication was examined by a measurement of the number of RNA copies in the medium using real-time RT-qPCR analysis (Reverse Transcription Quantitative Polymerase Chain Reaction). In the study, the MDCK cells were incubated for 2 days in a medium defined with DMEM without bovine serum. The infection was carried out in the presence of the polymer; after 2 hours, the medium was removed, and a fresh medium comprising polymers with proper concentrations was then introduced. The incubation was continued for 2 days. When incubation was completed, total RNA was isolated from the cell supernatants. After the reverse transcription reaction, cDNA was used as a matrix for the PCR.

Figure 6:
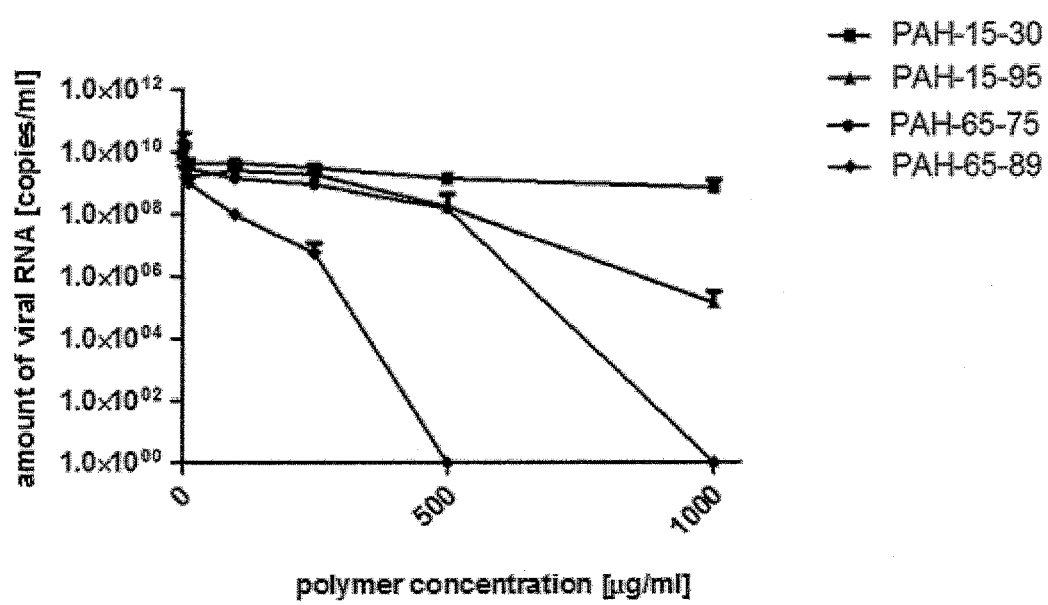
FIG. 6 shows the inhibition of replication of the influenza A virus (IAV) by the N-sulfonic polyallylamine derivatives, depending on the concentration, the degree of substitution with sulfonic groups and the molecular mass of the studied polymers.

The experiment was carried out using increasing concentrations of polymers. The obtained results are shown in FIG. 6 illustrating the inhibition of replication of the influenza A virus (IAV) by the N-sulfonic polyallylamine derivatives, depending on the concentration, the degree of substitution with sulfonic groups and the molecular mass of the studied polymers. The number of viral RNA copies was expressed as the number of RNA chains in 1 ml of the sample. Concentrations of the N-sulfonic polyallylamines, with which a 50% inhibition of replication of the influenza A virus (the so-called $IC_{50}$) was observed, are gathered in Table 6. It was observed that the N-sulfonic polyallylamine derivatives caused an inhibition of replication of the influenza A virus, while in the control samples (without the addition of the polymers), normal replication was found. A dependence of the antiviral effect vs. the degree of substitution with sulfonic groups and the molecular mass of the N-sulfonic polyallylamine derivatives was proven. The studies carried out indicate that the effect is stronger the higher the molecular mass is and the higher the degree of substitution of the polymer is. Non-modified polyallylamines (PAH-15 and PAH-65) did not exhibit antiviral properties, but at the same time they were highly toxic to MDCK and LLC-MK2 cell lines.

TABLE 6

Values of $IC_{50}$ determined based on the results of real-time PCR analysis (qRT-PCR).

| Polymer | Polymer concentration for $IC_{50}$ [µg/ml] |
|---|---|
| PAH-15-0 | — |
| PAH-65-0 | — |
| NSPAH-15-30 | 53.4 ± 1.7 |
| NSPAH-15-95 | 4.5 ± 2.1 |
| NSPAH-65-75 | 0.5 ± 1.2 |
| NSPAH-65-89 | 0.6 ± 1.1 |

LITERATURE REFERENCES CITED IN THE DESCRIPTION

[1] Ison, M., Johnston, S., Openshaw, P., Murphy, B., Hayden, F., Current research on respiratory viral infections: Fifth International Symposium1, Antiviral Research, 2004, 62, 75-110.

[2] Feuillet, F., Lina, B., Rosa-Calatrava, M., Boivin, G., Ten years of human metapneumovirus research. Journal of clinical virology: the official publication of the Pan American Society for Clinical Virology, 2012, 53: 97-105.

[3] http://www.lung.org/lung-disease/human-metapneumovirus/

[4] Ison, M. G., Antiviral therapies for respiratory viral infections in lung transplant patients, Antiviral therapy, 2012, 17, 193-200.

[5] Nichols, W. G., Peck C., Angela J., Boeckh, M., Respiratory viruses other than influenza virus: impact and therapeutic advances, Clinical microbiology reviews, 2008, 21, 274-290.

[6] Holme K. R., Perlin A. S., Chitosan N-sulfate (1997). A water-soluble polyelectrolyte. Carbohydrate Research. 302, 7-12.

[7] Knipe, D. & Howley, P., *Fields Virology. Sixth Edition*. (2013).

[8] Peltola, V. et al., Clinical effects of rhinovirus infections. *J. Clin. Viro.* 43, 411-414 (2008).

[9] Rahamat-Langendoen, J. C., Riezebos-Brilman, a, Hak, E., Scholvinck, E. H. & Niesters, H. G. M., The significance of rhinovirus detection in hospitalized children: clinical, epidemiological and virological features. *Clin. Microbiol. Infect.* 19, E435-42 (2013).

[10] Hayden, F. G., Advances in antivirals for non-influenza respiratory virus infections. *Influenza Other Respi. Viruses* 7, 36-43 (2013).

[11] Barnard, D. L. et al., In Vitro Activity of Expanded-Spectrum Pyridazinyl Oxime Ethers Related to Pirodavir: Novel Capsid-Binding Inhibitors with Potent Antipicornavirus Activity. *Antimicrob. Agents Chemother.* 48, 1766-1772 (2004).

[12] Abed, Y. & Boivin, G., Treatment of respiratory virus infections. *Antiviral Res.* 70, 1-16 (2006).

[13] Grassauer, A. et al., Iota-Carrageenan is a potent inhibitor of rhinovirus infection. *Virol. J.* 5, 107 (2008).

[14] Influenza (seasonal) (www.whoint/mediacentre/factsheets/fs211/en/), World Health Organization, April 2009, Retrieved Jan. 8, 2012

[15] Ballinger M. N., Standiford T. J., Postinfluenza bacterial pneumonia: host defenses gone awry, Journal of Interferon & Cytokine Research. September 2010, 30(9): 643-652.

[16] Vaccine virus selection for the 2012-2012 influenza season (http://www.cdc.gov/flu/about/season/vaccine-selection.htm), CDC publication updated 2 Jul. 2012, Retrieved 8 Aug. 2012.

[17] Quigley E., Influenza therapies: vaccines and antiviral drugs, Drug Discovery Today, 2006, 11: 478-480.
[18] Abed Y., Boivin G., Treatment of respiratory virus infections, Antiviral Research, 2006, 70: 1-16.
[19] Dreitlein W. B., Maratos J., Brocavich J., Zanamivir and oseltamivir: two new options for the treatment and prevention of influenza, Clinical Therapeutics, 2001, 23: 327-355.
[20] Leibbrandt A. et al., Iota-carrageenan is a potent inhibitor of influenza A virus infection, PLoS ONE, 2010, 5 (12): 14320.
[21] Bank S., New treatments for influenza, BMC medicine, 2012, 10: 104.
[22] Wei W., Zhang P. et al., Preparation and anti-influenza A virus activity of k-carrageenan oligosaccharide and its sulphate derivatives, Food Chemistry, 2012, 133: 880-888.
[23] Hosoya M. et al., Differential inhibitory effect of sulfated polysaccharides and polymers on the replication of various myxoviruses and retroviruses, depending on the composition of the target amino acid sequences of the viral envelope glycoproteins, Antimicrobial agents and chemotherapy, 1991, 35 (12): 2515-2520.
[24] Ikeda S., Neyts J. et al., In vitro and in vivo inhibition of Ortho- and paramyxovirus infections by a new class of sulfonic acid polymers interacting with virus-cell binding and/or fusion, Antimicrobial agents and chemotherapy, 1993, 38 (2): 256-259.

What is claimed is:

1. A method for treating and preventing infections caused by human metapneumoviruses hMPV, respiratory tract infections caused by the human rhinoviruses (HRV) and infections caused by the influenza A virus, comprising administering the anionically modified polyallylamine derivative (NSPAH) of the Formula 1 wherein each R is independently selected from $-SO_3^-$ and $-H$,
at least one R is $-SO_3^-$ group, and
n is an integer from 150 to 15000.

2. The method according to claim 1, wherein the anionically modified polyallylamine derivative is the form of a sodium salt.

3. The method according to claim 1, wherein the anionically modified polyallylamine derivative has the form of a solution or an aerosol administered to the upper respiratory tract.

* * * * *